United States Patent [19]

Okutani et al.

[11] Patent Number: 4,559,177
[45] Date of Patent: Dec. 17, 1985

[54] QUINONE DERIVATIVES

[75] Inventors: Tetsuya Okutani; Giichi Goto, both of Takatsuki, Japan

[73] Assignee: Takeda Chemical Industries, Ltd., Osaka, Japan

[21] Appl. No.: 164,018

[22] Filed: Jun. 30, 1980

[30] Foreign Application Priority Data

Jun. 28, 1979 [JP] Japan .................. 54-82381

[51] Int. Cl.$^4$ .............. C07C 50/28; C07C 69/007; C07C 69/145; C07C 69/78
[52] U.S. Cl. .................. 260/396 R; 560/144; 560/240; 560/254; 568/319; 568/337; 568/651; 514/826; 514/885; 260/408; 260/410.9 R; 260/413; 549/420
[58] Field of Search .............. 260/396 R; 424/308, 424/331, 311, 312

[56] References Cited

U.S. PATENT DOCUMENTS

| | | | |
|---|---|---|---|
| 3,658,852 | 4/1972 | Schuster et al. | 260/396 R |
| 3,859,317 | 1/1975 | Hutchings | 260/396 R |
| 3,966,776 | 6/1976 | Kato et al. | 260/396 R |
| 4,139,545 | 2/1979 | Morimoto et al. | 260/396 R |

FOREIGN PATENT DOCUMENTS

| | | |
|---|---|---|
| 2269333 | 11/1975 | France . |
| 2268778 | 11/1975 | France . |
| 2272068 | 12/1975 | France . |
| 2293194 | 7/1976 | France . |

*Primary Examiner*—Vivian Garner
*Attorney, Agent, or Firm*—Wenderoth, Lind & Ponack

[57] ABSTRACT

A compound of the formula:

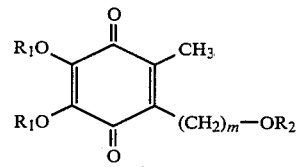

wherein m is an integer of 11 to 22; $R_1$ is alkyl having 1 to 4 carbon atoms; $R_2$ is hydrogen, alkyl having 1 to 4 carbon atoms or carboxylic acyl having 1 to 8 carbon atoms. Such compounds have pharmaceutical activities such as hypotensive, tissue metabolism stimulating, immuno-regulatory and lysosomal membrane stabilizing activity, and inhibit SRS-A production, and are useful as a heart failure remedy, cerebral circulation disturbance remedy, immuno-regulator, and antiallergic drug.

13 Claims, No Drawings

QUINONE DERIVATIVES

This invention relates to new quinone compounds of value as medicines and a novel method of producing quinone compounds.

Ubiquinones are effective against heart failure, periodontal disease, diabetes, muscular dystrophy, asthma, etc. but because they are generally low in water solubility, the route of administration is limited and the onset of action is not satisfactory. The research undertaken by us resulted in the finding of new quinone compounds which are possessed of desirable pharmacological activities and of a novel method for producing a quinone compound, which is advatnageous from the industrial point of view.

One aspect of the present invention relates to a quinone derivative of the formula

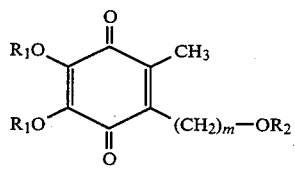

wherein m is an integer of 11 to 22; $R_1$ is lower alkyl having 1 to 4 carbon atoms; $R_2$ is hydrogen, lower alkyl having 1 to 4 carbon atoms or lower carboxylic acyl having 1 to 8 carbon atoms.

In the above formula (I), the lower alkyl designated by $R_1$ or $R_2$ is one having 1 to 4 carbon atoms, such as methyl, ethyl, n-propyl, n-butyl, etc. The lower carboxylic acyl designated by $R_2$ is one having 1 to 8 carbon atoms. As the embodiment of the lower carboxylic acyl $R_2$, there are mentioned formyl, alkylcarbonyl (e.g. acetyl, propionyl, butyryl, etc.), aralkylcarbonyl (e.g. phenylacetyl, etc.) and arylcarbonyl (e.g. benzoyl, etc.).

The present compound (I) has hypotensive, tissue metabolism-stimulating, immuno-regulatory, lysosomal membrane stabilizing and SRS-A (slow reacting substance of anaphylaxis) production inhibitory activities and is used as a heart failure remedy, cerebral circulation disturbance remedy, immuno-regulator, antiallergic drug (for the treatment of, e.g., asthma, rhinitis, etc.), etc. for mammalian animals including human beings. Useful dosage forms include capsules, granules, powders, tablets, troches, pills, syrup, injections, suppositories, etc. As an antiallergic drug, such dosage forms as ointment, aerosol, inhalation mist, etc. may be employed.

The pharmaceutically acceptable materials which can be used in formulating pharmaceutical preparations include, among others, excipients such as sucrose, lactose, glucose, starch, mannitol, sorbitol, cellulose, talc, cyclodextrin, etc.; binders such as cellulose, methylcellulose, polyvinyl pyrrolidone, gelatin, gum arabic, polyethylene glycol, sucrose, starch, etc.; disintegrators such as starch, carboxymethylcellulose, carboxymethylcellulose calcium salt, etc.; lubricants such as talc; flavorants; preservatives such as sodium benzoate; suspending agents such as methylcellulose, polyvinyl pyrrolidone, aluminum stearate, Polysorbate 80, Emalgen 408, Emasol 310, etc., solvents such as water, and such pharmaceutical bases as cacao butter, polyethylene glycol, witepsol, white petrolatum, etc. These materials are selectively used according to the type of pharmaceutical preparation.

The compound (I) of this invention is administered orally or otherwise, at doses of 5 to 500 mg, preferably 10 to 300 mg daily (0.1 to 10 mg/kg, preferably 0.2 to 6 mg/kg) for adult humans, for instance.

The present compound (I) can, for example, be prepared by oxidizing a compound of the formula

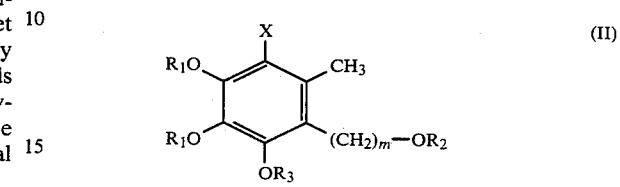

wherein the symbols $R_1$, $R_2$ and m have the same meanings given above; X is hydrogen, hydroxyl which may be protected or amino; $R_3$ is hydrogen, lower alkyl or lower carboxylic acyl.

In the above formula (II), lower alkyl designated by $R_3$ is one having 1 to 4 carbon atoms, such as methyl, ethyl, n-propyl, n-butyl, etc. The lower carboxylic acyl designated by $R_3$ is one having 1 to 8 carbon atoms. As the embodiment of the lower carboxylic acyl $R_3$, there are mentioned formyl, alkylcarbonyl (e.g. acetyl, propionyl, butyryl, etc.), aralkylcarbonyl (e.g. phenylacetyl, etc.) and arylcarbonyl (e.g. benzoyl, etc.). The protective group of the protected hydroxyl may be any protective group as long as it is easily cleaved chemically to give a free hydroxyl group. The examples of the protected hydroxyl X include alkoxy having 1 to 4 carbon atoms (e.g. methoxy, ethoxy, propoxy, butoxy, etc.), aralkyloxy having 7 to 9 carbon atoms (e.g. benzyloxy, etc.), carboxylic acyloxy having 1 to 8 carbon atoms (e.g. formylcarbonyloxy, alkylcarbonyloxy having 2 to 6 carbon atoms such as acetyloxy, propionyloxy, butyryloxy, aralkylcarbonyloxy having 8 to 10 carbon atoms such as phenylacetyloxy, arylcarbonyloxy having 7 to 9 carbon atoms such as benzoyloxy, etc.), acetal having 2 to 7 carbon atoms (e.g. tetrahydrofuranyloxy, tetrahydropyranyloxy, methoxymethyloxy, thiomethoxymethyloxy, etc.), trialkylsilyloxy having 3 to 6 carbon atoms (e.g. trimethylsilyloxy, t-butyldimethylsilyloxy, etc.), etc.

The oxidation is advantageously carried out by using an oxidizing agent. As the examples of the oxidizing agent, there are mentioned hydrogen peroxide; organic peracids, such as peracetic acid, performic acid, trifluoroperacetic acid, perbenzoic acid; metal oxides and their salts such as potassium permanganate, potassium perchromate, chromic anhydride, manganese dioxide, lead oxide, silver oxide, silver carbonate; sulfonic acid oxides such as potassium persulfate, anmonium persulfate; potassium nitrosodisulfonate; nitrites; ferric chloride; potassium ferrocyanide; etc.

The oxidation is conventionally conducted in the presence of a solvent. Any solvent which does not prevent the oxidation reaction can be used. The embodiments of the solvent include water, aqueous solutions containing acid or base; alcohols such as methanol, ethanol, butanol, etc.; aliphatic ketones such as acetone, methylethylketone, etc.; ethers such as dioxane, tetrahydrofuran, ethyl ether, etc.; halogenated hydrocarbons such as chloroform, dichloromethane, 1,2-dichloroethane, tetrachloromethane, etc.; amides such as dimethylformamide, dimethylacetamide, hexamethylphosphoroamide, dimethyl sulfoxide, etc.

The reaction temperature is usually in the range of 10° C. to the boiling point of the solvent, and the reaction time is preferably 0.5 hour to about 10 days, though they vary depending on the kind of oxidizing agent.

In case that persulfate or nitrite is used as an oxidizing agent, it is preferable to conduct the oxidation reaction in the presence of a suitable buffer solution such as phosphate buffer solution.

After the oxidation reaction, the product compound can be easily isolated and purified by procedures known per se (e.g. extraction, concentration, recrystallization, chromatography, etc.).

The other aspect of the present invention relates to a method of producing a quinone derivative of the general formula:

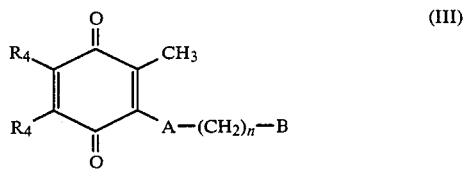

[wherein each $R_4$ is lower alkyl having 1 to 4 carbon atoms or lower alkoxy having 1 to 4 carbon atoms, or two $R_4$'s taken together represent —CH=CH—CH=CH—; n is zero or an integer of 1 to 20 and when n is 1 to 20, A is —$CH_2$—,

or —CO— and B is hydroxymethyl, carboxylic acyloxymethyl having 2 to 11 carbon atoms, esterified or unesterified carboxyl having 1 to 5 carbon atoms, lower alkoxymethyl having 2 to 5 carbon atoms, trialkyl silyloxymethyl having 4 to 7 carbon atoms or acetalmethyl having 3 to 8 carbon atoms; when N is zero, —A—$(CH_2)_N$—B is

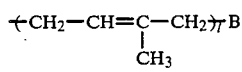

wherein l is zero or an integer of 1 to 12 and B is H], which comprises oxidizing a compound of the general formula:

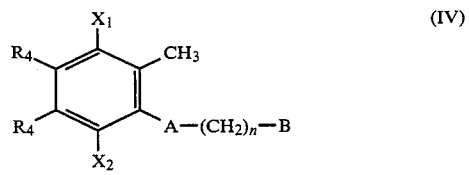

[wherein either $X_1$ or $X_2$ is hydroxyl or amino, with the other being H, an esterified hydroxyl having 1 to 8 carbon atoms or etherified hydroxyl having 2 to 8 carbon atoms; the other symbols are as defined above] with oxygen or air in the presence of a transition metal complex compound.

It is known that a quinone derivative of general formula (III) can be obtained by oxidizing a compound of general formula (IV) with an oxidizing agent such as hydrogen peroxide, peracetic acid, performic acid, potassium dichromate, potassium permanganate, chromic anhydride, potassium nitrosodisulfonate, potassium persulfate and so on. However, when an oxidizing agent such as those mentioned above is employed, the desired compounds can be obtained only in low yield and the by-products are produced in large amounts so that the desired compounds are hardly of high purity. Moreover, using the above-mentioned oxidizing agents in large amounts is not desirable from a safety point of view. Thus, the conventional processes are not suited for commercial production purposes. In contrast, the method of this invention employs a transition metal complex compound and yields the desired compounds in good yield and purity, thus being very advantageous for commercial-scale production.

Referring to the above general formulas (III) and (IV), the lower alkyl group $R_4$ may be a straight-chain or branched alkyl group containing 1 to 4 carbon atoms each, such as methyl, ethyl, n-propyl, i-propyl, n-butyl, i-butyl, etc. The alkoxy group, also designated by $R_4$, may be a group of 1 to 4 carbon atoms, such as methoxy, ethoxy, n-propoxy, n-butoxy, etc. The symbol n is zero or an integer of 1 to 20, preferably, zero or 10 to 20, and most preferably 13 to 20. The symbol i is zero or an integer of 1 to 12 and preferably 3 to 12. The lower carboxylic acyloxymethyl group B is one having 2 to 11 carbon atoms, and may be formyloxymethyl, alkylcarbonyloxymethyl group of 3 to 6 carbon atoms, preferably of 3 to 5 carbon atoms, e.g. acetyloxymethyl, n-propionyloxymethyl, n-butyryloxymethyl, etc.; an arylcarbonyloxymethyl group of 8 to 9 carbon atoms, e.g. phenylcarbonyloxymethyl, p-methylphenylcarbonyloxymethyl, etc.; or an aralkylcarbonyloxymethyl group of 9 to 11 carbon atoms, e.g. benzylcarbonyloxymethyl, phenethylcarbonyloxymethyl, etc. The optionally esterified carboxyl group B may for example be a free carboxyl group, or an alkoxycarbonyl group of 2 to 5 carbon atoms, e.g. methoxycarbonyl, ethoxycarbonyl, n-propoxycarbonyl, n-butoxycarbonyl, etc. The lower alkoxymethyl group B may be a group of 2 to 5 carbon atoms, e.g. methoxymethyl, ethoxymethyl, n-propoxymethyl, n-butoxymethyl, etc. The trialkyl silyloxymethyl group B may be a group having 4 to 7 carbon atoms, e.g. trimethylsilyloxymethyl, t-butyldimethylsilyloxymethyl, etc. The acetalmethyl group B may be a group having 3 to 8 carbon atoms, e.g. tetrahydropyranyloxymethyl, tetrahydrofuranyloxymethyl, methoxymethyloxymethyl, methylthiomethyloxymethyl, etc. The esterified or etherified hydroxyl group, which is designated by $X_1$ or $X_2$, may for example be a carboxylic acyloxy group, such as alkylcarbonyloxy groups of 2 to 6 carbon atoms, preferably of 2 to 4 carbon atoms (e.g. acetyloxy, propionyloxy, butyryloxy, etc.), arylcarbonyloxy groups having 6 to 8 carbon atoms (e.g. benzoyloxy), etc., tetrahydrophyranyloxy, tetrahydrofuranyloxy, alkoxyalkyloxy groups (the carbon numbers of alkoxy and alkyl are 1 to 7 and 1 to 2, respectively) such as methoxymethyloxy, 2-methoxyethyloxy, etc., trialkylsilyloxy having 3 to 6 carbon atoms such as trimethylsilyloxy, t-butyldimethylsilyloxy, etc.

The oxidation reaction according to this invention is carried out by catalytic oxidation reaction with oxygen, air or the like in the presence of a transition metal complex compound. The transition metal complex compound is a complex compound which is able to reversibly yield an oxygen complex compound on interaction with oxygen, such as the complex compounds of iron, cobalt, nickel, copper, etc., although complex compounds of cobalt are particularly desirable. Of such complex compounds of cobalt, compounds represented by the following general formula are preferred.

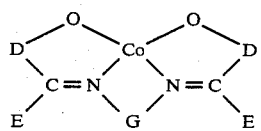

[wherein D is a vinylene group of

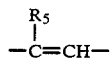

($R_5$ is lower alkyl or phenyl) or an orthophenylene group of

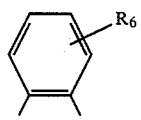

($R_6$ is H, hydroxy or lower alkoxy); E is H or lower alkyl; G is an ethylene group of

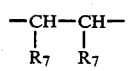

($R_7$ is H or lower alkyl) or an orthophenylene group of

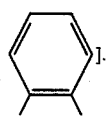

The lower alkyl groups $R_5$, $R_7$ and E is one having 1 to 2 carbon atoms and include methyl, ethyl, etc.; the lower alkoxy group $R_6$ in one having 1 to 2 carbon atoms and may for example be methoxy or ethoxy. As examples of compounds having the above general formula (V), there may be mentioned such divalent cobalt-Schiff's base complexes such as cobalt salen (salcomine), cobalt salpr, cobalt salphen, cobalt acacen, cobalt bzacen and such other compounds as bis(3-alkoxysalicylidene)ethylenediiminocobalt(II), bis(4-hydroxysalicylidene)ethylenediiminocobalt(II), etc.

This catalytic oxidation reaction is usually conducted in an organic solvent. The solvent includes, for example, halogenated hydrocarbons such as dichloromethane, 1,2-dichloroethane, 1,1,2,2-tetrachloroethane, chloroform, carbon tetrachloride, etc.; lower alcohol-type organic solvents such as methanol, ethanol, butanol, etc.; amide-type solvents such as dimethylformamide, dimethylacetamide, hexamethylphosphorotriamide, etc.; pyridine and substituted pyridine (e.g. s-collidine), dimethylsulfoxide, sulfolane, etc. These organic solvents can be used as a mixture of two or more species.

The amount of metal complex compound used in accordance with this invention should vary with the type of substrate compound and other conditions of reaction. Usually, the complex compound is used in a range of 0.01 to 50 weight percent relative to compound (IV) and, preferably, 1 to 30 weight percent on the same basis. The oxidation reaction with the aid of this complex compound is promoted by the addition of imidazole, pyridine or cyanide ion (e.g. sodium cyanide). The amount of such an additive is preferably the same as that of the transition metal complex.

The reacton temperature is normally in the range of 0° C. to 80° C. and, preferably, room temperature. This reaction may be conducted at atmospheric pressure and, optionally, at an elevated pressure not over 150 atms. The reaction time may range from 0.5 hour to 30 days normally up to 75 hours.

After the oxidation reaction, the product compound can be easily isolated and purified by procedures known per se (e.g. extraction, concentration, recrystallization, chromatography, etc.).

The starting compound (IV) used in the practice of the present invention can be produced, for example, by the method described in U.S. Pat. No. 4,139,545 or a method analogous thereto. The compound (IV) can also be produced through the following steps.

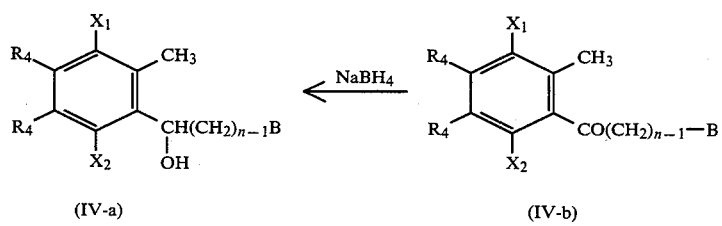

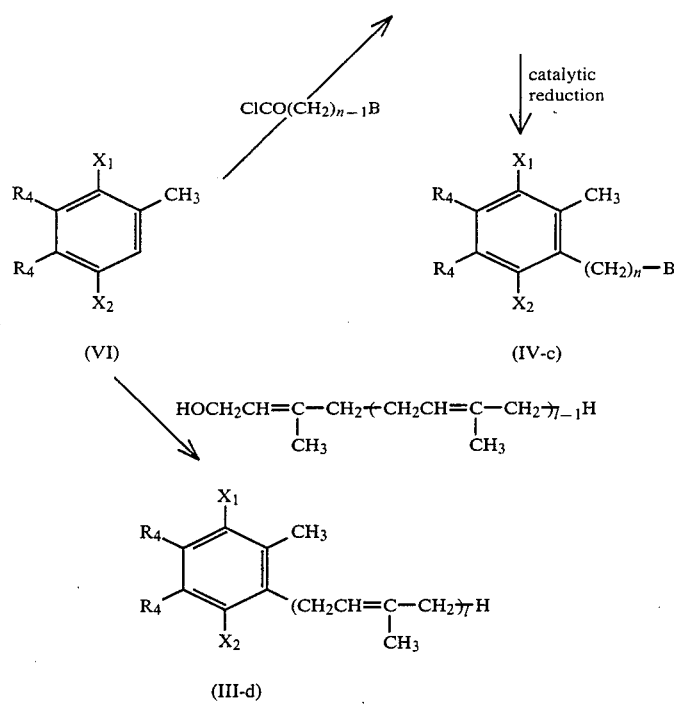

(III-d)

In the above formulas, each symbol is as defined hereinbefore.

EXAMPLE 1

2,3-dimethoxy-5-methyl-1,4-benzoquinone (1.7 g) is dissolved in acetic acid (20 ml), and while the solution is stirred at 90° C., bis-13-methoxycarbonyltridecanoyl peroxide (7.6 g) is added in small increments. The temperature of the mixture is kept for 22 hours. After cooling the mixture is diluted with water and subjected to extraction with ether. The extract is washed with a saturated aqueous solution of sodium chloride, an aqueous solution of sodium hydrogen carbonate and an aqueous solution of sodium chloride in the order mentioned, and dried. The solvent is distilled off and the residue is recrystallized from hexane. The above procedure gives 2,3-dimethoxy-6-(12-methoxycarbonyldodecyl)-5-methyl-1,4-benzoquinone as orange-colored needles. Melting point: 54° C.

Lithium aluminum hydride (740 mg) is suspended in dry ether (80 ml) and to the suspension is added dropwise a solution of 2,3-dimethoxy-5-methyl-6-(12-methoxycarbonyldodecyl)-1,4-benzoquinone (1.06 g) in dry ether (100 ml) under ice-cooling and stirring. After 1.5 hour, ice-water is added to the mixture to decompose excess lithium aluminum hydride. The mixture is acidified with hydrochloric acid and subjected to extraction with ether. The extract is washed with water and concentrated under a reduced pressure. The residue is dissolved in methanol (30 ml) and to the solution is added a solution of ferric chloride (12 g) in water (60 ml) and the mixture is stirred at room temperature for 1.5 hour. The reaction mixture is diluted with water and subjected to extraction with ethyl acetate. The extract is washed with water, and dried. The solvent is distilled off under reduced pressure. The residue is dissolved in chloroform and subjected to column chromatography on silica gel. The crystals obtained from the first-emerging fraction eluted with chloroformethanol (99:1) is recrystallized from ether-hexane. The above procedure yields 6-(13-hydroxytridecyl)-2,3-dimethoxy-5-methyl-1,4-benzoquinone as yellow needles. (727 mg) Melting point 65°–66° C.

EXAMPLE 2

To a solution of methyl 22-(2-hydroxy-3,4-dimethoxy-6-methylphenyl)docosanoate (3 g) in tetrahydrofuran (30 ml) is added lithium aluminum hydride and the mixture is stirred at room temperature for 1 hour. Under ice-cooling, 10% aqueous solution of sulfuric acid is added to the reaction mixture. The mixture is subjected to extraction with ether. The extract is washed with water and dried. The solvent is distilled off under reduced pressure, whereby 6-(22-hydroxydocosyl)-2,3-dimethoxy-5-methylphenol is obtained as colorless needles. m.p. 78° C.–81° C.

Elemental analysis: calculated for $C_{31}H_{54}O_4$ C, 75.87; H, 11.09. Found C, 75.79; H, 11.38.

22-(2-hydroxy-3,4-dimethoxy-6-methylphenyl)-docosanl-ol (300 mg) and bis(4-hydroxysalicylidene)ethylenediiminocobalt(II) (50 mg) are suspended in dimethylformamide (200 ml). The mixture is stirred in oxygen gas streams at atmospheric temperature and pressure for 7 days. The insolubles are filtered off and the filtrate is concentrated under reduced pressure. The residue is diluted with water and subjected to extraction with ethyl acetate. The extract is treated in a conventional manner and subjected to column chromatography on silica gel. Fractions eluted with chloroform are collected and the solvent is distilled off under reduced pressure. The residue is subjected to recrystallization, whereby 6-(22-hydroxydocosyl)-2,3-dimethoxy-5-methyl-1,4-benzoquinone is obtained as orange-yellow needles. Melting point 89° C.–90.5° C.

EXAMPLE 3

To a solution of 12-acetoxy-n-dodecanoyl chloride (8.5 g) in 1,2-dichloroethane (30 ml) is added aluminum chloride (8.2 g) and the mixture is stirred at room temperature for 2 hours. The mixture is cooled to 5° C. and a solution of 3,4,5-trimethoxytoluene (5.6 g) in 1,2-dichloromethane (20 ml) is added to the above mixture. The mixture is stirred at room temperature for 72 hours, and at 50° C.–60° C. for 30 minutes. Methanol (200 ml) is added to the reaction mixture and the mixture is stirred at 50° C. for 3 hours. The solvent is distilled off, and the residue is subjected to extraction with dichloromethane. The dichloromethane layer is washed with water and dried over magnesium sulfate. The solvent is distilled off to thereby leave crude crystals. The product is recrystallized from ether-hexane (1:1) to give 6-(12-hydroxy-1-oxododecyl)-2,3-dimethoxy-5-methylphenol (8.5 g) as colorless needles. Melting point 82° C.

To a solution of 6-(12-hydroxy-1-oxodecyl)-2,3-dimethoxy-5-methylphenol (6.4 g) in acetic acid (150 ml) are added 5% palladium-carbon (50% hydrous) (1.1 g) and 70% perchloric acid (0.1 ml) and the mixture is subjected to the catalytic reduction at atmospheric temperature and pressure. After the absorption of hydrogen has been completed, the catalyst is filtered off and the filtrate is concentrated under reduced pressure. The residue is extracted with dichloromethane and the dichloromethane layer is washed with a 5% aqueous solution of sodium hydrogen carbonate and dried over anhydrous magnesium sulfate. The solvent is distilled off to give 6-(12-acetoxydodecyl)-2,3-dimethoxy-5-methylphenol (6.8 g) as a colorless oil.

IR$\nu_{max}^{Neat}$ cm$^{-1}$: 3450 (OH), 1730 (OAc), 1610, 1580 (Ar).

NMR$\delta_{ppm}^{CDCl_3}$: 1.1–1.8 [20H, m, —(CH$_2$)$_{10}$—], 2.02(3H, s, OAc), 2.23(3H, s, C$_5$—CH$_3$), 2.55 (2H, t, J=7 Hz, C$_1$—H$_2$), 3.79(3H, s, OCH$_3$), 3.83(3H, s, OCH$_3$), 4.02(2H, t, J=6 Hz, CH$_2$OAc), 5.78(1H, s, C$_1$—OH), 6.23(1H, s, C$_4$—H) MS m/e: 394(M$^+$), 352, 334, 181.

To a solution of 6-(12-acetoxydodecyl)-2,3-dimethoxy-5-methylphenol (6.1 g) in dimethylformamide (300 ml) are added nitrosodisulfonate (18 g), water (300 ml), methanol (50 ml) and monopotassium phosphate (0.5 g) and the mixture is stirred at room temperature for 30 days. The reaction mixture is subjected to extraction with dichloromethane and the organic layer is washed with water and dried over magnesium sulfate. The solvent is distilled off to thereby leave crude crystals. The product is recrystallized from hexane to give 6-(12-acetoxydodecyl)-2,3-dimethoxy-5-methyl-1,4-benzoquinone (4.8 g) as orange-yellow needles.

Melting point: 47° C.

To a solution of 6-(12-acetoxydodecyl)-2,3-dimethoxy-5-methyl-1,4-benzoquinone (4.4 g) in methanol (200 ml) is added concentrated hydrochloric acid (0.1 ml) and the mixture is kept standing at room temperature for 12 hours. To the reaction mixture is added sodium hydrogen carbonate (0.2 g), and the solvent is distilled off. The residue is dissolved in dichloromethane and the insoluble materials are filtered off. Dichloromethane is distilled off to thereby leave crude crystals. Recrystallization from hexane-ether (3:1) gives 6-(12-hydroxydodecyl)-2,3-dimethoxy-5-methyl-1,4-benzoquinone (3.8 g) as orange-yellow needles. Melting point: 63° C.

IR$\nu_{max}^{KBr}$ cm$^{-1}$: 3550(OH), 1650, 1640, 1610(1,4-benzoquinone).

NMR$\delta_{ppm}^{CDCl_3}$: 1.1–1.8 [20H, m, —(CH$_2$)$_{10}$—], 2.00(3H, s, C$_5$—CH$_3$), 2.43(2H, t, J=7 Hz, C$_1$—H$_2$), 3.62(2H, t, J=6 Hz, CH$_2$OH), 3.97(6H, s, OCH$_3 \times 2$).

MS m/e: 366(M$^+$), 368(M$^+$+2), 336, 338, 197, 196, 195.

EXAMPLE 4

To a solution of 6-(20-hydroxyeicosyl)-2,3-dimethoxy-5-methylphenol (2.3 g) in dimethylformamide (1.5 l) are added potassium nitrosodisulfonate (30 g), water (1.5 l), methanol (300 ml) and monopotassium phosphate (1.3 g) and the mixture is stirred at room temperature for 45 days. The reaction mixture is extracted with dichloromethane and recrystallized from ether. The above procedure gives 6-(20-hydroxyeicosyl)-2,3-dimethoxy-5-methyl-1,4-benzoquinone (1.3 g) as yellow needles. Melting point: 85° C.

IR$\nu_{max}^{KBr}$ cm$^{-1}$: 3500(OH), 1660, 1640, 1610 (1,4-benzoquinone).

NMR$\delta_{ppm}^{CDCl_3}$: 1.1–1.8 [36H, m, —(CH$_2$)$_{18}$—], 2.00(3H, s, C$_5$—CH$_3$), 2.43(2H, t, J=7 Hz, C$_1$—H$_2$), 3.62(2H, t, J=6 Hz, —CH$_2$OH), 3.96(6H, s, OCH$_3 \times 2$).

MS m/e: 478(M$^+$), 480(M$^+$+2), 448, 450, 197, 196, 195.

EXAMPLE 5

To a solution of 6-(20-hydroxyeicosyl)-2,3-dimethoxy-5-methylphenol (0.6 g) in tetrahydrofuran is added a solution of potassium persulfate (2.7 g) in water (20 ml), the mixture is stirred in nitrogen gas streams at room temperature for 72 hours. The reaction product is extracted with ether and ether is distilled off. To the residual 6-(20-hydroxyeicosyl)-2,3-dimethoxy-5-methylhydroquinone is added acetic anhydride (1 ml) and the mixture is kept standing at room temperature for 3 hours. The reaction mixture is extracted and treated in a conventional manner. The crude product thus obtained is recrystallized from hexane. The above procedure to give 6-(20-acetoxyeicosyl)-2,3-dimethoxy-5-methylhydroquinone-1,4-diacetate (0.31 g) as colorless needles. Melting point: 67° C.

By a similar manner to the corresponding procedure of Example 3, the product obtained above is treated with methanolic concentrated hydrochloric acid and then treated with methanolic ferric chloride, whereby 6-(20-hydroxyeicosyl)-2,3-dimethoxy-5-methyl-1,4-benzoquinone is obtained. m.p.: 85° C.

EXAMPLE 6

To a solution of 6-(11-acetoxyundecyl)-2,3-dimethoxy-5-methylphenol (8 g) in dimethylformamide (400 ml) are added potassium nitrosodisulfonate (24 g), water (400 ml), methanol (30 ml) and monopotassium phosphate (1.0 g). The mixture is stirred at room temperature for 28 days. The reaction product is extracted with dichloromethane and the dichloromethane layer is washed with water and dried over magnesium sulfate. The solvent is distilled off to thereby leave crude crystals. The crude crystals are recrystallized from hexane to yield 6.4 g of 6-(11-acetoxyundecyl)-2,3-dimethoxy-5-methyl-1,4-benzoquinone as orange-yellow needles, m.p.: 41° C.

To a solution of 6-(11-acetoxyundecyl)-2,3-dimethoxy-5-methyl-1,4-benzoquinone (4.2 g) in methanol (200 ml) is added concentrated sulfuric acid (0.1 ml) and the mixture is kept standing at room temperature for 12 hours. To a reaction mixture is added potassium hydrogencarbonate (0.2 g) and the solvent is distilled off. The resultant is dissolved in dichloromethane and insolubles are filtered off. Dichloromethane is distilled off to leave crude crystals. Recrystallization from hexane-ether (3:1) gives 6-(11-hydroxyundecyl)-2,3-dimethoxy-5-methyl-1,4-benzoquinone (3.6 g) as orange-yellow needles. m.p.: 57° C.

EXAMPLE 7

To a dimethylformamide solution (50 ml) of 6-(10-hydroxydecyl)-2,3-dimethoxy-5-methylphenol (2.53 g) is added bis(salicylidene)ethylenediiminocobalt(II) (salcomine) (0.1 g) and the mixture is stirred in oxygen streams at atmospheric temperature and pressure for 72 hours. The solvent is then distilled off and the product is extracted with ether. The ethereal layer is washed with water and dried over anhydrous sodium sulfate, and the solvent is distilled off. The above procedure yields 6-(10-hydroxydecyl)-2,3-dimethoxy-5-methyl-1,4-benzoquinone (2.32 g) as orange-yellow needles melting at 52° C.

EXAMPLE 8

To a dimethylformamide solution (100 ml) of 6-(10-hydroxydecyl)-2,3-dimethoxy-5-methylphenol (4.1 g) is added bis(3-methoxysalicylidene)ethylenediiminocobalt(II) (0.2 g) and the mixture is stirred in oxygen streams at atmospheric temperature and pressure for 72 hours. After the reaction has been completed, the solvent is distilled off and the residue is extracted with ether. The ethereal layer is washed with water and dried, and the solvent is distilled off in the conventional manner. The crude crystals thus obtained are recrystallized from ethyl acetate-hexane (1:3). The above procedure yields 6-(10-hydroxydecyl)-2,3-dimethoxy-5-methyl-1,4-benzoquinone (3.77 g) as orange-yellow needles melting at 52° C.–53° C.

EXAMPLE 9

To a dimethylformamide solution (30 ml) of 6-(10-acetoxydecyl)-2,3-dimethoxy-5-methylphenyl (1.6 g) is added bis(salicylidene)ethylenediiminocobalt(II) (0.05 g) and the mixture is stirred in oxygen streams at atmospheric temperature and pressure for 72 hours. After the reaction has been completed, the solvent is distilled off and the product is isolated in the same manner as described in Example 7. The crude crystals thus obtained are recrystallized from hexane. The above procedure yields 6-(10-acetoxydecyl)-2,3-dimethoxy-5-methyl-1,4-benzoquinone (1.32 g) as orange-yellow needles melting at 38° C.

EXAMPLE 10

To a dichloromethane solution (30 ml) of 6-(10-hydroxydecyl)-2,3-dimethoxy-5-methylphenol (1.4 g) is added bis(salicylidene)ethylenediiminocobalt(II) (0.06 g), and the mixture is stirred in oxygen streams at 20° C. and atmospheric pressure for 72 hours. After the reaction has been completed, the reaction mixture is passed through a bed of a small quantity of silica gel (about 15 g) to remove the catalyst. The solvent is then distilled off and the residue is recrystallized from ether-hexane (1:4). The above procedure yields 6-(10-hydroxydecyl)-2,3-dimethoxy-5-methyl-1,4-benzoquinone (1.01 g) as orange-yellow needles melting at 51° C.–52° C.

EXAMPLE 11

To a dimethylformamide solution (30 ml) of 6-(10-hydroxydecyl)-2,3-dimethoxy-5-methylphenol (1.6 g) are added bis(3-methoxysalicylidene)ethylenediiminocobalt(II) (0.06 g) and pyridine (10 mg), and the mixture is stirred in air streams at atmospheric temperature and pressure for 72 hours. After the reaction has been completed, the reaction product is isolated in the same manner as described in Example 7. The crude crystals thus obtained are recrystallized from ether-hexane (1:3). The above procedure yields 6-(10-hydroxydecyl)-2,3-dimethoxy-5-methyl-1,4-benzoquinone (1.1 g) as orange-yellow needles melting at 51° C.–53° C.

EXAMPLE 12

To a dichloromethane solution (30 ml) of 6-(9-hydroxynonyl)-2,3-dimethoxy-5-methylphenol (1.8 g) are added pyridine (0.5 ml) and bis(salicylidene)ethylenediiminocobalt(II) (32 mg). The mixture is stirred in oxygen streams at atmospheric temperature and pressure. The reaction product is isolated as in Example 7 and recrystallized from hexane. The above procedure yields 6-(9-hydroxynonyl)-2,3-dimethoxy-5-methyl-1,4-benzoquinone (1.2 g) as orange-yellow needles melting at 45° C.

EXAMPLE 13

To a dimethylformamide solution (20 ml) of 6-(6-hydroxyhexyl)-2,3-dimethoxy-5-methylphenol (1.5 g) is added bis(salicylidene)ethylenediiminocobalt(II) (15 mg), and the mixture is stirred in oxygen streams at atmospheric temperature and pressure for 72 hours. The reaction product is isolated as in Example 7 and purified by silica gel column chromatography. The ether-hexane (1:1) eluate yields 6-(6-hydroxyhexyl)-2,3-dimethoxy-5-methyl-1,4-benzoquinone (1.1 g) as orange-yellow oil.

Infrared absorption spectrum $\nu_{max}^{Neat}$ cm$^{-1}$: 3400(OH), 1660, 1640, 1610 (1,4-benzoquinone).

Mass spectrum, m/e: 282(M$^+$), 284(M$^+$+2), 252, 197, 196, 195.

EXAMPLE 14

To a dimethylformamide solution (30 ml) of 6-(12-hydroxydodecyl)-2,3-dimethoxy-5-methylphenol (1.7 g) are added pyridine (50 mg) and bis(4-hydroxysalicylidene)ethylenediiminocobalt(II) (36 mg), and the mixture is stirred in oxygen streams at atmospheric temperature and pressure for 72 hours. The reaction product is isolated as in Example 7 and recrystallized from ether. The above procedure yields 6-(12-hydroxydodecyl)-2,3-dimethoxy-5-methyl-1,4-benzoquinone (1.37 g), m.p. 63° C.

EXAMPLE 15

To a dimethylformamide solution (20 ml) of 6-(12-acetoxydodecyl)-2,3-dimethoxy-5-methylphenol (1.1 g) is added bis(salicylidene)ethylenediiminocobalt(II) (40 mg) and the mixture is stirred in oxygen streams at atmospheric pressure and temperature for 72 hours. The product is isolated as in Example 7 and recrystallized from etherhexane (1:1). The above procedure yields 6-(12-acetoxydodecyl)-2,3-dimethoxy-5-methyl-1,4-benzoquinone (0.84 g) as orange-yellow needles melting at 47° C.

EXAMPLE 16

To a dimethylformamide solution (50 ml) of 6-(20-hydroxyeicosanyl)-2,3-dimethoxy-5-methylphenol (4.0 g) is added bis(salicylidene)ethylenediiminocobalt(II) (40 mg), and the mixture is stirred in oxygen streams at atmospheric temperature and pressure for 72 hours. The product is isolated as in Example 7 and recrystallized from ether. The above procedure yields 6-(20-hydroxyeicosyl)-2,3-dimethoxy-5-methyl-1,4-benzoquinone (3.28 g) as yellow needles melting at 85° C.

EXAMPLE 17

To a methanol solution (30 ml) of 6-(9-acetoxynonyl)-2,3-dimethoxy-5-methylphenol (1.1 g) are added pyridine (0.3 ml) and bis(salicylidene)ethylenediiminocobalt(II) (14 mg), followed by stirring in oxygen streams at atmospheric temperature and pressure for 72 hours. The reaction product is isolated as in Example 7 and recrystallized from hexane. The above procedure yields 6-(9-acetoxynonyl)-2,3-dimethoxy-5-methyl-1,4-benzoquinone as orange-yellow needles melting at 30° C.

EXAMPLE 18

To a dimethylformamide solution (10 ml) of 1-acetoxy-6-(10-acetoxydecyl)-2,3-dimethoxy-5-methylbenzene (179 mg) are added bis(salicylidene)ethylenediiminocobalt(II) (10 mg) and sodium cyanide (2 mg) followed by stirring in oxygen stream at atmospheric temperature and pressure for 96 hours. After the reaction has been completed, 10 to 30 mg of ferric chloride is added to make the sodium cyanide-iron complex and, thereafter, the desired compound is isolated in the same manner as Example 7. Recrystallization of the product from hexane yields 6-(10-acetoxydecyl)-2,3-dimethoxy-5-methyl-1,4-benzoquinone (103 mg) as orange-yellow needles melting at 37° C.-38° C.

EXAMPLE 19

To a dimethylformamide solution (20 ml) of 6-(10-acetoxydecyl)-2,3-dimethoxy-5-methyl-1-tetrahydropyranyloxybenzene (240 mg) is added bis(salicylidene)ethylenediiminocobalt(II) (14 mg), followed by stirring in oxygen streams at atmospheric temperature and pressure for 72 hours. The reaction product is isolated in the same manner as Example 7 and recrystallized from hexane. The above procedure yields 6-(10-acetoxydecyl)-2,3-dimethoxy-5-methyl-1,4-benzoquinone (110 mg) as orange-yellow needles melting at 37° C.-38° C.

EXAMPLE 20

To a dimethylformamide solution of 10-(3,4-dimethoxy-2-hydroxy-6-methylphenyl)decanoic acid (100 mg) is added bis(salicylidene)ethylenediiminocobalt(II) (10 mg), followed by stirring in oxygen streams at atmospheric temperature and pressure for 72 hours. The desired compound is isolated in the same manner as Example 7 and recrystallized from ether. The above procedure yields 6-(9-carboxynonyl)-2,3-dimethoxy-5-methyl-1,4-benzoquinone (78 mg) as orange-yellow needles melting at 59° C.-60° C.

EXAMPLE 21

A dimethylformamide solution of methyl 10-(3,4-dimethoxy-2-hydroxy-6-methylphenyl)decanoate (129 mg) is oxidized in the same manner as Example 20. This procedure yields 2,3-dimethoxy-5-methyl-6-(9-methoxycarbonylnonyl)-1,4-benzoquinone (91 mg) as orange-yellow needles melting at 37° C.-38° C.

EXAMPLE 22

10-(2-Hydroxy-3,4,6-trimethylphenyl)decanoic acid (270 mg) is oxidized in the same manner as Example 7. This procedure yields 2,3,5-trimethyl-6-(9-carboxynonyl)-1,4-benzoquinone (200 mg) as orange-yellow oil.

IR spectrum $\nu_{max}^{Neat}$cm$^{-1}$: 1705(COOH), 1640, 1610(quinone).

EXAMPLE 23

1-(2-Hydroxy-3,4,6-trimethylphenyl)-1,6-hexanediol (331 mg) is oxidized in the same manner as Example 7 to obtain 2,3,5-trimethyl-6-(1,6-dihydroxyhexyl)-1,4-benzoquinone (229 mg) as orange-yellow oil.

IR spectrum $\nu_{max}^{Neat}$cm$^{-1}$: 3400(OH), 1640, 1610 (quinone).

EXAMPLE 24

To a dimethylformamide solution (30 ml) of 2,3-dimethoxy-5-methylphenol (3 g) is added bis(salicylidene)ethylenediiminocobalt(II) (35 mg) and the mixture is reacted and worked up in the same manner as Example 7. The resultant crude crystals are recrystallized from hexane. The above procedure yields 2,3-dimethoxy-5-methyl-1,4-benzoquinone (2.13 g) as orange-yellow needles melting at 59° C.-60° C.

EXAMPLE 25

To a dimethylformamide solution (35 ml) of 2,3,4-trimethoxy-6-methyl aniline (3.4 g) is added bis(salicylidene)ethylenediiminocobalt(II) (120 mg), followed by stirring in oxygen streams at atmospheric temperature and pressure for 72 hours. The reaction product is isolated in the same manner as Example 7 and recrystallized from hexane. The above procedure yields 2,3-dimethoxy-5-methyl-1,4-benzoquinone (2.9 g) as orange-yellow needles melting at 59° C.-60° C.

EXAMPLE 26

To dry toluene (40) are added 4-methoxy-3-methyl-1-naphthol (1.88 g) and potassium hydride (401 mg) followed by refluxing in nitrogen streams for an hour. After spontaneous cooling, geranyl bromide (1.95 g) is added and the mixture is stirred at room temperature for 24 hours. To the reaction mixture is added petroleum ether (100 ml) and the precipitated potassium bromide is filtered off and the solvent is distilled off at room temperature and under reduced pressure. The residue is dissolved in dimethylformamide (50 ml) followed by addition of bis(salicylidene)ethylenediiminocobalt(II) (100 mg). The mixture is stirred in oxygen gas streams at atmospheric temperature and pressure for one hour, after which the product is extracted with ether. The ethereal layer is washed with water and dried over anhydrous sodium sulfate, followed by distillation removal of the solvent. The residue is fractionally purified by silica gel column chromatography (developing solvent:ether-petroleum ether=1:19). The crude crystals thus obtained are recrystallized from acetone-alcohol. The above procedure yields menaquinone-2 (1.45 g) as yellow needles melting at 51° C.-53° C.

EXAMPLE 27

To a solution of 18-acetoxy-n-octadecanoyl chloride (11 g) in 1,2-dichloroethane (50 ml) is added aluminum chloride (7 g) and the mixture is stirred at room temperature for 2 hours. This reaction mixture is cooled to 5° C. and a solution of 3,4,5-trimethoxytoluene (6.2 g) in 1,2-dichloroethane (20 ml) is added. The mixture is stirred at room temperature for 72 hours. Then, this reaction mixture is heated to 50° C.–60° C. and stirred for 30 minutes. After cooling, ice-water is added to the reaction mixture and the product is extracted with dichloromethane. The dichloromethane layer is washed with water and the solvent is distilled off to recover an oil (12.1 g). This oil is dissolved in methanol (150 ml) followed by addition of sodium hydroxide (5.2 g). The mixture is stirred at room temperature for 2 hours, at the end of which time it is neutralized with 5N-HCl and the solvent is distilled off. The resultant crude crystals are rinsed with water and recrystallized from dichloromethane-ether (1:1). The above procedure yields 6-(18-hydroxy-1-oxooctadecyl)-2,3-dimethoxy-5-methylphenol (6.4 g) as colorless needles, m.p. 101° C.

To a solution of 6-(18-hydroxy-1-oxooctadecyl)-2,3-dimethoxy-5-methylphenol (1.4 g) in acetic acid (30 ml) are added 5% palladium-on-carbon (50% hydrous) (0.5 g) and 70% perchloric acid (0.05 ml), and catalytic reduction is carried out at atmospheric temperature and pressure. After the absorption of hydrogen has subsided, the catalyst is filtered off and the filtrate is concentrated under reduced pressure, whereupon a colorless oil is obtained. This product is dissolved in ether and the ether layer is washed with 5% aqueous solution of sodium hydrogen carbonate and dried over anhydrous sodium sulfate. The solvent is then distilled off and the resultant crude crystals are recrystallized from hexane. The above procedure yields 6-(18-acetoxyoctadecyl)-2,3-dimethoxy-5-methylphenol (1.4 g) as colorless needles, m.p. 53° C.

The above 18-acetoxy compound was deacetylated by the corresponding procedure of Example 6 and the resultant 6-(18-hydroxyoctadecyl)-2,3-dimethoxy-5-methylphenol (0.5 g) is dissolved in dimethylformamide (1 l). To this solution is added potassium nitrosodisulfonate (13 g), 700 ml of water, 100 ml of methanol and monopotassium phosphate (1 g), and the mixture is stirred at room temperature for 45 days. The product is extracted in the conventional manner and recrystallized from ether-hexane. The above procedure yields 6-(18-hydroxyoctadecyl)-2,3-dimethoxy-5-methyl-1,4-benzoquinone as yellow needles (0.31 g), m.p. 81° C.

Elemental analysis for $C_{27}H_{46}O_5$: Calcd. C, 71.96; H, 10.29. Found C, 72.06; H, 10.27.

What is claimed is:

1. A compound of the formula:

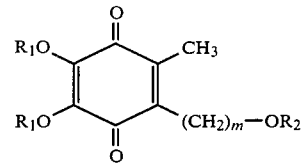

wherein m is an integer of 11 to 22; $R_1$ is alkyl having 1 to 4 carbon atoms; and $R_2$ is hydrogen, alkyl having 1 to 4 carbon atoms or carboxylic acyl having 1 to 8 carbon atoms.

2. A compound as claimed in claim 1, wherein $R_2$ is hydrogen.

3. A compound as claimed in claim 1, wherein $R_2$ is carboxylic acyl having 1 to 8 carbon atoms.

4. A compound as claimed in claim 1, wherein $R_1$ is methyl.

5. A compound as claimed in claim 1, wherein m is an integer of 11 to 13.

6. A compound as claimed in claim 1, wherein the compound is 6-(13-hydroxytridecyl)-2,3-dimethoxy-5-methyl-1,4-benzoquinone.

7. A compound as claimed in claim 1, wherein the compound is 6-(22-hydroxydocosyl)-2,3-dimethoxy-5-methyl-1,4-benzoquinone.

8. A compound as claimed in claim 1, wherein the compound is 6-(12-hydroxydodecyl)-2,3-dimethoxy-5-methyl-1,4-benzoquinone.

9. A compound as claimed in claim 1, wherein the compound is 6-(11-hydroxyundecyl)-2,3-dimethoxy-5-methyl-1,4-benzoquinone.

10. A compound as claimed in claim 1, wherein the compound is 6-(20-hydroxyeicosyl)-2,3-dimethoxy-5-methyl-1,4-benzoquinone.

11. A compound as claimed in claim 1, wherein the compound is 6-(12-acetoxydodecyl)-2,3-dimethoxy-5-methyl-1,4-benzoquinone.

12. A compound as claimed in claim 1, wherein the compound is 6-(11-acetoxyundecyl)-2,3-dimethoxy-5-methyl-1,4-benzoquinone.

13. A compound as claimed in claim 1, wherein the compound is 6-(18-hydroxyoctadecyl)-2,3-dimethoxy-5-methyl-1,4-benzoquinone.

* * * * *